United States Patent [19]
Allen et al.

[11] Patent Number: 4,880,628
[45] Date of Patent: * Nov. 14, 1989

[54] SUSTAINED RELEASE COMPOSITION

[75] Inventors: William M. Allen, Reading; Bernard F. Sansom, Newbury; Alan D. Wilson, Liphook; Havard J. Prosser, Royston; David M. Groffman, Harrow, all of England

[73] Assignee: National Research Development Corporation, England

[ * ] Notice: The portion of the term of this patent subsequent to Apr. 28, 2004 has been disclaimed.

[21] Appl. No.: 17,272

[22] Filed: Feb. 20, 1987

Related U.S. Application Data

[63] Continuation of Ser. No. 707,958, Mar. 4, 1985, Pat. No. 4,661,339, which is a continuation of Ser. No. 513,774, Jul. 14, 1983, abandoned.

[30] Foreign Application Priority Data

Jul. 20, 1982 [GB] United Kingdom ................ 8220969
May 31, 1983 [GB] United Kingdom ................ 8314888

[51] Int. Cl.$^4$ ............................................. A61K 33/18
[52] U.S. Cl. .................................... 424/605; 424/400; 424/409; 424/646; 424/667; 424/702
[58] Field of Search ............... 424/127, 128, 131, 140, 424/141, 143, 145, 147, 150, 154, 162, 400, 409

[56] References Cited

U.S. PATENT DOCUMENTS

| | | |
|---|---|---|
| 3,056,724 | 10/1962 | Marston . |
| 3,804,794 | 4/1974 | Schmitt et al. . |
| 4,447,254 | 5/1984 | Hughes et al. . |
| 4,661,339 | 4/1987 | Allen et al. ......................... 424/486 |

FOREIGN PATENT DOCUMENTS

| | | |
|---|---|---|
| 1542092 | 2/1972 | Fed. Rep. of Germany . |
| 2432688 | 3/1975 | Fed. Rep. of Germany . |
| 2612273 | 9/1976 | Fed. Rep. of Germany . |
| 2652163 | 1/1978 | Fed. Rep. of Germany . |
| 1176196 | 1/1970 | United Kingdom . |

OTHER PUBLICATIONS

Carroll et al.–Chem. Abst., vol. 48(1954), p. 12381a.

Primary Examiner—Sam Rosen
Attorney, Agent, or Firm—Jacobs & Jacobs

[57] ABSTRACT

A sustained release device which comprises a source of at least one trace chemical element incorporated in a cement and releasable therefrom on contact with an aqueous medium.

The trace chemical element is exemplified by selenium, cobalt and iodine and the cement is exemplified by a phosphate cement.

14 Claims, No Drawings

SUSTAINED RELEASE COMPOSITION

CROSS-REFERENCE

This is a continuation of Ser. No. 707,958 filed Mar. 4, 1985 now U.S. Pat. No. 4,661,339 which is a continuation of Ser. No. 513,774 filed July 14, 1983, abandoned.

This invention relates to sustained release devices; more particularly, this invention relates to such devices which provide sustained release of active substances, especially substances having a medicinal effect. The invention is of particular, but not exclusive, relevance to animal husbandry.

During the last half-century it has become increasingly clear that, in order to maintain a complete, balanced metabolism, healthy livestock requires trace but sustained amounts of a number of chemical elements. Furthermore, ever more intensive systems of animal husbandry dictate that these requirements have to be rigorously adhered to.

In the Preliminary Table below, approximate minimum requirements, expressed in ppm. of dry dietary matter of certain chemical elements, are given (from "The Mineral Nutrition of Livestock" second edition, by E. J. Underwood published by the Commonwealth Agricultural Bureaux). It is to be understood that dietary requirements vary with the species and breed of animal, its age, its rate of growth or production and with the biological availability of the chemical element.

| CHEMICAL ELEMENT | PRELIMINARY TABLE LIVESTOCK | | | |
| --- | --- | --- | --- | --- |
| | PIGS | POULTRY | SHEEP | CATTLE |
| Mg | 325–500 | 200–600 | 700 | 700[1] |
| Fe | 50–125 | 40–80 | 25–40 | 25–40 |
| I | 0.05–0.14 | 0.05–0.14 | 0.05–0.14 | 0.03–0.8 |
| Cu | 6[2] | 3–6 | 1–10 | 8–14 |
| Co | — | — | 0.7–1.1 | 0.7–1.1 |
| Mn | 12–40 | 25–108 | 10–40 | 10–25 |
| Zn | 35–46 | 35–65 | 17–33 | 30–50 |
| Se | 0.03–0.1 | 0.01–0.28 | 0.03–0.12 | 0.03–0.12 |

([1]If dietary magnesium (as presented) is available for metabolism only to the extent of 20%, then the magnesium requirements for a 40-liter cow can be as much as 24 g.day$^{-1}$, especially in the spring.)
([2]Copper requirements are powerfully influenced by interaction with other dietary components, especially molybdenum and sulphur.)

This invention seeks to provide a device which can give sustained release of one or more active substances, especially substances having a medicinal effect in a form preferably, but not necessarily, for oral administration or parenteral implant, not requiring frequent dosing and which can be susceptible of extempore preparation by a local veterinary surgeon.

Accordingly, the present invention provides a sustained release device which comprises a source of at least one trace chemical element, optionally with at least one active substance other than a trace chemical element, incorporated in a cement and releasable therefrom on contact with an aqueous medium. At least one trace chemical element may be an intrinsic component of the cement and/or at least one trace chemical element may be dispersed in the cement.

Such devices have also been found suitable for uses other than in oral administration or parenteral implant in livestock and where sustained release is desired, for example in the provision of one or more active substances in agriculture or horticulture. Examples include the sustained provision of magnesium for tomato crops or of copper as an antifouling agent for combating marine growth.

The term "active substance" as used herein includes any substance the administration of which to a locus imparts to that locus an effect which is beneficial to human resources. The effect imparted may be an enhancement of a desired effect (e.g. the improved health and/or rate of growth of livestock attained by correct provision of trace chemical elements) or the reduction or eradication of an undesired effect. The locus will be in vivo in the case of livestock but this need not be the case, for example, in agriculture or horticulture.

The term "substance having a medicinal effect" as used herein incudes any active substance other than a trace chemical element the administration of which in vivo has a prophylactic or therapeutic effect.

By "trace chemical element" is meant herein at least one of As, B, Cd, Co, Cr, Cu, F, Fe, I, Mg, Mn, Mo, Ni, Se, Si, Sn, V or Zn. This does not imply that the devices of this invention may only release these elements in trace amounts; on the contrary, magnesium needs to be released in substantial amounts in cattle, as noted above; furthermore, other elements, such as Cu, may be required to be released in substantial amounts in uses other than oral administration or parenteral implant to livestock.

The term "cement" as used herein means the coherent mass formed by reaction at a temperature below 250° C., preferably below 100° C., especially at ambient temperature, from at least one settable substance (but excludes covalently cross-linked organic thermoset materials) rather than the cement-forming component(s) themselves. It is desirable that the settable substance is capable of adhesively binding solid particles by its setting about those particles though, in accordance with this invention, the solid particles need not always be or remain present.

The cement may be a hydraulic cement: that is, one in which the cement-forming component(s) are settable to form the cement by the action of water; for example, the various Portland cements (including ordinary, rapid-hardening, quick-setting and white) and pozzolanic cements. Preferably, however, the cement is a reaction cement: that is, one in which at least two cement-forming components other than water are reactable to form the cement. Preferably, the cement is an acid-base reaction cement: that is, one in which at least one cement-forming component is a Lewis or Bronsted acid and at least one other cement-forming component is a Lewis or Bronsted base. Examples include acid phosphate, phosphate, nitrate, sulphate, selenate, selenite (oxychalcogenate), and oxychloride cements.

In the preferred case of acid-base reaction cements the cement is suitably formed from an acid cement-forming component which comprises a mineral acid, an acid salt, a Lewis acid, a polyfunctional organic carboxylic acid, a polyfunctional organic phosphoric acid, a polyfunctional phenol, a homo- or co-polymer of an unsaturated carboxylic acid, a homo- or co-polymer of an unsaturated sulphonic acid, or a hydrolysable precursor thereof. The term "hydrolysable precursor" as used herein includes any species, such as an anhydride or an acid chloride, which is transformed on hydrolysis to the required acid cement-forming component. Suitable examples of mineral acids include phosphoric acids such as orthophosphoric acid, pyro-phosphoric acid and meta-phosphoric acids, sulphuric acid, nitric acid, and hydrohalic acids, such as hydrochloric acid, with phosphoric acids being preferred. Examples of acid salts include the hydrogen and dihydrogen phosphates; bisulphates, and bifluorides, especially the alkali metal hydrogen and dihydrogen phosphates. Examples of Lewis acids include those metal halides which are Lewis acids, such as aluminium trichloride, aluminium tribromide, magnesium chloride, magnesium iodide, ferric chloride, zinc chloride, zinc iodide and copper chloride. Others are oxyacid salts, such as sulphates, selenates and selenites. Examples of polyfunctional organic carboxylic acids, polyfunctional organic phosphoric acids and polyfunctional phenols include the following polybasic acids: malonic, mesoxalic, succinic, glutaric, adipic, pimelic, suberic, azelaic, sebacic, malic, citric, tartaric, tartronic, tricarballylic, maleic, fumaric, citraconic, mesaconic, itaconic, glutaconic, muconic, aconitic, ortho-, iso- and tere-phthalic, gallic, tannic and mellitic acids, phytic acid, catechol, resorcinol, quinol, pyrogallol, hydroxyquinol and phloroglucinol. Other polyfunctional organic carboxylic acids and phenols which are not polybasic but are suitable as acid cement-forming components include hydroxycarboxylic acids and ketoacids. Examples are lactic, pyruvic, 2-hydroxyisobutyric, 2-hydroxycyclohexane carboxylic, 2-hydroxy-2-phenyl propionic, diphenylhydroxyacetic, 2-hydroxybenzoic, 3-hydroxybenzoic and 4-hydroxybenzoic acids, eugenol and salicylaldehyde. Examples of homo- or co-polymers of an unsaturated carboxylic acid include those prepared by the homopolymerisation or copolymerisation of aconitic acid, acrylic acid, citraconic acid, fumaric acid, glutaconic acid, itaconic acid, maleic acid, mesaconic acid, methacrylic acid, muconic acid and tiglic acid, and the copolymerisation of these acids with other unsaturated aliphatic monomers for example vinyl monomers, such as vinyl hydrocarbon monomers, vinyl ethers, acrylamide or acrylonitrile. Particularly noteworthy are the homopolymers of acrylic acid and its copolymers, particularly copolymers of acrylic acid and itaconic acid, especially those described and claimed in UK 1484454. Good results have also been obtained using a copolymer of vinyl methyl ether and maleic acid. Examples of homo- or co-polymers of an unsaturated sulphonic acid include those prepared by the homopolymerisation or copolymerisation of ethylene sulphonic acid.

It is also possible to use a hydrolysable precursor of such polymers, for example a poly(carboxylic acid anhydride); furthermore, polyacrylic acids may be prepared by hydrolysis of corresponding polyacrylonitriles. The hydrolysable precursor of a poly(carboxylic acid) may be a homopolymer of an unsaturated carboxylic acid anhydride or a copolymer with an above mentioned other carboxylic acid or anhydride thereof, or a copolymer of an unsaturated carboxylic acid anhydride with an unsaturated aliphatic monomer, for example vinyl monomers, such as vinyl hydrocarbon monomers, linear or cyclic vinyl ethers, acrylamide or acrylonitrile, for example pyran copolymer. Good results may be obtained by using homopolymers of maleic anhydride or vinyl orthophthalic anhydride, or copolymers thereof, especially block copolymers thereof, with ethylene, propylene, butenes, styrene and vinyl methyl ether. Mixtures of such components may be used. Preferably, the acid cement-forming component is in aqueous solution.

The acid-base reaction cement is also suitably formed from a base cement-forming component which comprises a basic or amphoteric oxide or hydroxide, or a salt of a weak or volatile acid. There are many basic or amphoteric oxides or hydroxides which can form cements with at least one of the acid-cement forming components defined above; examples include $Li_2O$ (other Group IA oxides or hydroxides tend to give materials which are too soluble in aqueous media, although they can be incorporated in minor amounts to facilitate release in other cements), Group IIA oxides, preferably calcined, such as MgO, "$Ti(OH)_4$", "$Zr(OH)_4$", $V_2O_5$, $Fe_2O_3$, $Cu_2O$, CuO, ZnO, preferably calcined, $Al_2O_3 \times H_2O$ and SnO. Salts of weak or volatile acids include carbonates, monocarboxylates, such as acetates, and halides, such as the halides of Mg, Ca, Ba, Th, Ti, Zr, Al and Sn. They also include the extensive class of monomeric and polymeric (alumino)silicates, (alumino)phosphates and (alumino)borates which include the acid-reactive natural and synthetic minerals and ion-leachable glasses. By "(alumino)silicate" is meant herein a silicate or an aluminosilicate; by "(alumino)phosphate" is meant herein a phosphate or an aluminophosphate; by "(alumino)borate" is meant herein a borate or an aluminoborate. Examples of ion-leachable glasses include those glasses wherein the principal acidic oxide is silica (although the glass may also contain minor amounts of other anhydrides such as phosphorus pentoxide and boric oxide), and wherein the principal basic oxide in the glass is alumina which, although it has amphoteric properties, can be considered for the purposes of the present invention solely as a basic oxide. Particularly preferred glasses fall within the composition range of 10 to 65% w/w silica and 15 to 50% w/w alumina. The glass desirably contains at least one other basic oxide, preferably calcium oxide, which may be present in the glass composition in an amount from 0 to 50% w/w. The calcium oxide may be partly or wholly replaced by sodium oxide or other basic oxide or a mixture of basic oxides. The presence of sodium oxide can be desirable in increasing the solubility of the resulting cement. Preferred glasses for use in the present invention containing alumina, silica and calcium oxide are the gehlenite and anorthite glasses, and in general glasses falling within the composition range 10 to 65% w/w silica, 15 to 50% w/w alumina and 0 to 50% w/w calcium oxide.

Other glasses suitable for use in the present invention may contain fluoride, suitably up to 15% by weight, preferably less than 10% by weight. A class of fluoraluminosilicate glasses particularly suited to this invention are those wherein the ratio by weight of silica to alumina is from 1.5 to 2.0 and the ratio by weight of fluorine to alumina is from 0.6 to 2.5, or wherein the ratio by weight of silica to alumina is from 0.5 to 1.5 and the ratio by weight of fluorine to alumina is from 0.25 to 2.0.

Mixtures of such components may be used.

It is noted that, apart from cement-forming components of unequivocal acidity or basicity, certain components may react as acid cement-forming components under a given set of reaction conditions while reacting as base cement-forming components under a different set of reaction conditions.

The present invention is of broad applicability in the formulation of trace chemical elments releasable at a sustained rate.

This invention is particularly suited to sustained provision of sources of one or more of the following trace chemical elements: Mg, Fe, I, Cu, Co, Mn, Zn or Se, especially of at least one of Cu, Co, Se or I.

The source of trace chemical element may preferably be a phosphate, especially acid phosphate cement, a basic halide, a basic chalcogenate, or a carboxylate cement. Oxyhalide cements are of particular value in the sustained provision of halogen, especially iodine. Oxychalcogenate cements have values both in provision of cationic sources, for example of copper and cobalt in oxysulphate cements as well as anionic sources, for example, of selenium in oxyselenate cements.

Furthermore, it is possible to disperse one or more sources of trace chemical elements in cements which are themselves sources of one or more (or indeed no) other or the same chemical elements. Where they are other chemical elements they need not be trace chemical elements. In this manner it is possible to get a multisource device with all sources releasing a sustained, appropriate amount. Moreover, it is also possible to vary the dosage, in accordance with this invention, to suit local conditions and also to incorporate at least one active substance other than a trace chemical element, especially one having a medicinal effect.

Examples of classes of active substance other than a trace chemical element which may be additionally incorporated in the sustained release devices of the present invention include pharmaceuticals, bacteriostats, viruscides, herbicides, pesticides such as insecticides, nematicides, and larvicides, fungicides, topical or dermatological agents, proteins, for example enzymes, peptides, vaccines, growth promoting factors used in agriculture, horticulture and animal husbandry, for example fertilisers, vitamins, for example nicotinamide and anabolic steroids. Of particular interest are compositions of the present invention comprising, as active substance, at least one substance having a medicinal effect.

Specific classes of substance having a medicinal effect which may be utilised in a sustained release device of the invention include hypnotics, sedatives, tranquilisers, antipyretics, antiinflammatory agents, antihistamines, antitussives, anticonvulsants, muscle relaxants, topical or dermatological agents, antispasmodics, anti-ulcer agents, preparations containing various substances for the treatment of infection by pathogens including antifungal agents, antiparasitic agents such as anthelmintics; for example avermectin and morantel tartrate, and other antimicrobials such as antibiotics; for example oxytetracycline, preparations containing hormones, for example androgenic, estrogenic and progestational hormones, notably steroids, such as progesterone, trenbolone, oestradiol and polypeptide hormones, sympathomimetic agents, hypoglycaemic agents, nutritional agents, preparations containing enzymes of various types of activity, for example chymotrypsin, preparations containing analgesics, for example aspirin and agents with many other types of action including nematocides and other agents of veterinary application. Mixtures of active substances may be incorporated into the sustained release devices of the invention which may suitably comprise a dosage from, especially one which is an integral body of cement.

In order to ensure retention of oral dosage sustained release devices of this invention in the reticulo-rumen of ruminant stock, it is desirable to incorporate therein a weighting agent to raise the density of the device, typically to about 3, although a somewhat lower density may be appropriate. The weighting agent may be dispersed throughout the device (e.g. as iron filings) or consolidated (e.g. as an essentially coaxially positioned steel rod).

The configuration of the sustained release devices of the invention is selected having regard both to the desired release characteristics and ease of administration. The devices are most often used in the form of a shaped body such as a hollow or blank cylinder, a sphere, a tablet or a slab and the nature of the shape and its dimensions may be selected appropriately. A primary target is to achieve a sustained release over appropriate time period, conveniently of a major proportion, for example 80 or 90%, of the active substance. Unusual release profiles may, however, be obtained by utilising devices which comprise open cavities, for example hollow cylinders or slabs with one or more holes or hollows in them. It is found that the release profiles of such devices can go through a maximum with time. Such geometric control of release profiles provides very useful additional means of obtaining and controlling improved release profiles. It is preferred, however, that the device is a cylindrical dosage form which may be mono- or bis-spherically capped. For administration orally to sheep this may be up to 20 mm in diameter and 50 mm long; for administration orally to cattle this may be up to 35 mm in diameter and 160 mm long. For parenteral administration either to sheep or cattle cylinders 3 mm in diameter and 5 mm long are very suitable. Up to 4 in sheep and 10 in cattle may be incorporated in one implant.

In accordance with a further aspect of this invention, there is provided a process for the preparation of a device of the invention, which process comprises preparing a cement-forming mixture in which is incorporated a source of at least one trace chemical element; investing a mould with the mixture; and permitting the cement-forming mixture to cure in the mould, preferably wherein the cement is subjected to a post-curing treatment at an elevated temperature.

However, it is also within the scope of the present invention to utilise the cement in powdered form optionally in suspension in a liquid medium (for example as a subcutaneous depot).

In accordance with a further aspect of this invention, there is provided a particulate composition reactable in the presence of a polar liquid, suitably water, to form a device as herein defined.

This invention also provides a pack which comprises a particulate composition, a polar liquid, suitably water, reactable with the composition to form a device as herein defined, and separating means to prevent accidental reaction of the particulate composition with the polar liquid.

This invention further provides a source of at least one trace chemical element, optionally with at least one active substance other than a trace chemical element, incorporated in a cement, or a particulate composition reactable in the presence of, or with, a polar liquid to form the same, for use in prophylaxis or therapy. In particular, the invention provides magnesium incorporated in a cement, or a particulate composition reactable in the presence of, or with, a polar liquid to form the same, for use in the prophylaxis or therapy of grass tetany, especially in lactating cows and ewes. The invention provides iron incorporated in a cement, or a particulate composition reactable in the presence of, or with, a polar liquid to form the same, for use in the prophylaxis or therapy of anaemia, especially in sucking pigs. The invention also provides iodine incorporated in a cement, or a particulate composition reactable in the presence of, or with, a polar liquid to form the same, for use in the prophylaxis of goitre. The invention further provides copper incorporated in a cement, or a particulate composition reactable in the presence of, or with, a polar liquid to form the same, to facilitate anabolism in young pigs or ruminants. The invention provides cobalt incorporated in a cement, or a particulate composition reactable in the presence of, or with, a polar liquid to form the same, for use in the prophylaxis or therapy of subclinical retardation or enzootic marasmus in sheep or cattle. The invention also provides manganese incorporated in a cement, or a particulate composition reactable in the presence of, or with, a polar liquid to form the same, for use in the prophylaxis or therapy of perosis or nutritional chondrodystrophy in poultry or manganese deficiency in ruminants.

This invention provides livestock whenever administered with a sustained release device or an active substance as herein defined.

This invention further provides a cement in which a plurality of trace metals is incorporated. The oxyselenate and acid phosphate cements are also novel products of the invention.

In a preferred embodiment, the invention provides a cement in which sources of Cu, Co and Se are incorporated. The invention also provides an integral body of a cement comprising at least one trace chemical element and, dispersed therein, at least one different trace chemical element and/or at least one active substance other than a trace chemical element.

The following Examples illustrate the invention. Parts are by weight unless otherwise stated. All numerical values given are the mean of two determinations.

EXAMPLE 1

This Example describes the preparation and testing of cylindrical devices of magnesium phosphate cement designed to release magnesium as prophylaxis or therapy for grass tetany in ruminant stock.

Two sources of base cement-forming component were used:
(i) magnesium oxide calcined at 1000° C. (ex White Sea & Baltic Co.); and
(ii) a magnesium aluminosilicate glass prepared by fluxing together 180 parts magnesium carbonate, 180 parts silica and 100 parts alumina (all ex BDH Chemicals).

Three sources of orthophosphoric acid (ex Fisons, AR grade) solution as acid cement-forming component were used:
(iii) 60% w/w aqueous orthophosphoric acid comprising 3.0% w/w aluminium;
(iv) 50% w/w aqueous orthophosphoric acid comprising 2.5% w/w aluminium; and
(v) 50% w/w aqueous orthophosphoric acid comprising no aluminium.

The components were mixed together at the ratio shown in Table 1a below and were packed into cylindrical moulds 12 mm×6 mm diameter. These were then sealed for 16 hours at 37° C. to form cylindrical devices. A pH=5 buffer solution was next prepared from sodium acetate/acetic acid. The cylindrical devices were incorporated in the buffer solution and the in vitro release of magnesium was monitored with a Pye Unicam SP 1950 atomic absorption spectrophotometer. Results at pH=5 are shown in Table 1b.

TABLE 1a

| Cement | base component (powder) | acid component (liquid) | powder:liquid ratio (g/ml) | setting time (h) 23° C. and 50% RH | compressive strength after 24 h (MPa) |
| --- | --- | --- | --- | --- | --- |
| 1 | (i) | (iii) | 3.0 | 4 | 191 |
| 2 | (i) | (iv) | 3.0 | 4 | 100 |
| 3 | (i) | (v) | 3.0 | 1 | 71 |
| 4 | (ii) | (iv) | 3.5 | 2 | 149 |
| 5 | (ii) | (iii) | 3.5 | 6.5 | 2 |

TABLE 1b

| | Mg leached/day (% w/w of cement) | | | | | | | | | |
| --- | --- | --- | --- | --- | --- | --- | --- | --- | --- | --- |
| Cement | after 1 d | 2 d | 3 d | 4 d | 5 d | 6 d | 7 d | 14 d | 21 d | 28 d |
| 4 | 0.11 | 0.057 | 0.039 | 0.032 | 0.074 | 0.056 | 0.047 | 0.028 | 0.023 | 0.028 |
| 1 | 0.56 | 0.52 | 0.49 | 0.54 | 0.53 | 0.47 | 0.46 | 0.50 | 0.42 | 0.93 |

EXAMPLE 2

This Example describes the preparation and testing of cylindrical devices of magnesium oxychloride or magnesium oxysulphate cement.

Three sources of base cement-forming component were used:
(i) magnesium oxide (heavy, ex Hopkin and Williams) heated at 40° C. for 18 h;
(ii) magnesium carbonate (ex BDH Chemicals) heated to 650° C. for 6 h; and
(iii) magnesium carbonate heated to 850° C. for 6 h.

Two sources of acid cement-forming components were used:
(iv) 30% w/v aqueous magnesium chloride (ex Fisons) solution; and
(v) 22.4% w/v magnesium sulphate (ex Fisons) solution.

The components were mixed together at a powder:liquid ratio of 4 g:5 ml; moulded; and tested at pH=5 in essentially the same manner as described in Example 1. The results are shown in Table 2.

TABLE 2

| Cement | base ponent | acid component | Mg leached/day (% w/w of cement) after 1 d | 8 d | 15 d | Average weight loss/day (% w/w of cement) |
| --- | --- | --- | --- | --- | --- | --- |
| 6 | (i) | (iv) | 1.50 | 1.35 | 0.30 | 6.7 |
| 7 | (ii) | (iv) | 1.76 | 1.38 | 0.74 | 6.3 |

TABLE 2-continued

| Cement | base ponent | acid com- ponent | Mg leached/day (% w/w of cement) after 1 d | 8 d | 15 d | Average day (% w/w of cement) |
|---|---|---|---|---|---|---|
| 8 | (iii) | (iv) | 1.64 | 1.63 | 0.70 | 6.2 |
| 9 | (i) | (v) | 2.03 | 2.18 | — | 9.1 |
| 10 | (ii) | (v) | 3.72 | 1.88 | — | 8.0 |
| 11 | (iii) | (v) | 2.56 | 1.64 | — | 6.3 |

EXAMPLE 3

This Example describes the preparation of larger cylindrical devices comprising a weighting agent.

In this Example, components (i), (iv) and (v) of Example 2 and component (iii) of Example 1 were used. They were mixed, essentially as in Example 1 at a powder:liquid ratio of 4 g:5 ml. Pure iron (99%) powder (ex Goodfellow Metals Ltd.) was also admixed as a weighting agent. The mixture was then packed into cylindrical moulds of 20 mm×12 mm diameter and 20 mm×20 mm diameter, cured and tested at the pH shown in essentially the same manner as described in Example 1. The results are shown in Table 3. Inter alia, they show that the rate of release of Mg is pH dependent with the rate increasing rapidly with decreasing pH.

TABLE 3

| Cement | Magnesium oxide: liquid:Fe | pH of leaching solution | Mg leached/day (% w/w of cement) after 1 d | 2 d | 3 d | 4 d | 5 d | 6 d | 7 d | 8 d | original wt (g) | wt. after (g) | % av. weight loss |
|---|---|---|---|---|---|---|---|---|---|---|---|---|---|
| 12[1] | 4:5[3]:15.5 | 5 | 1.203 | 0.864 | 0.717 | 0.673 | 0.647 | 0.557 | 0.502 | 0.489 | 20.206 | 11.560 | 5.35 |
|  |  | 6 | 0.454 | 0.106 | 0.094 | 0.086 | 0.058 | 0.056 | 0.055 | 0.052 | 20.086 | 19.406 | 0.423 |
|  |  | 5.5–6.0[6] | 0.368 | 0.219 | 0.133 | 0.087 | — | — | — | — | 19.678 | 18.719 | 1.22 |
| 13[1] | 2.4:5[3]:15.5 | 5 | 1.237 | 0.635 | 0.543 | 0.411 | — | — | — | — | 20.07 | 14.585 | 6.83 |
|  |  | 6 | 0.389 | 0.118 | 0.089 | 0.060 | — | — | — | — | 20.035 | 17.606 | 3.03 |
| 14[1] | 4:5[4]:15.5 | 5 | 0.732 | 0.678 | 0.641 | 0.615 | 0.577 | 0.556 | 0.507 | 0.474 | 20.365 | 12.749 | 4.67 |
|  |  | 6 | 0.185 | 0.090 | 0.075 | 0.69 | 0.85 | 0.063 | 0.060 | 0.060 | 21.111 | 20.632 | 0.284 |
| 15[1] | 3.5:3[4]:15.5 | 5 | 1.315 | 0.757 | 0.602 | 0.411 | — | — | — | — | 17.909 | 12.688 | 7.29 |
|  |  | 6 | 0.476 | 0.163 | 0.131 | 0.097 | — | — | — | — | 18.373 | 17.090 | 1.75 |
|  |  | 5.5–6.0[6] | 0.601 | 0.245 | 0.167 | 0.136 | — | — | — | — | 18.003 | 16.109 | 2.63 |
| 16[2] | 3:1[5]:6.25 | 5 | 1.183 | 0.737 | 0.408 | 0.304 | 0.228 | 0.193 | 0.175 | 0.100 | 5.886 | 5.394 | 1.04 |
|  |  | 6 | 0.154 | 0.114 | 0.092 | 0.090 | 0.119 | 0.083 | 0.081 | 0.078 | 6.549 | 6.506 | 0.082 |

[1] of dimensions 20 mm × 20 mm diameter
[2] of dimensions 20 mm × 12 mm diameter
[3] liquid (iv) of Example 2
[4] liquid (v) of Example 2
[5] liquid (iii) of Example 1
[6] distilled demineralised water at a pH from 5.5 to 6.0

EXAMPLE 4

This Example describes in vivo testing of the cements described in Example 3.

Cylindrical devices, prepared as described in Example 3 and of the dimensions shown in Table 4, were simply inserted into the reticulum of a cow having a fistulated rumen. Periodically the devices were removed, weighed and replaced.

TABLE 4

| Cement | device dimensions (mm) | initial wt. (g) | % loss of original weight per day Cow J629 after 10 d | 20 d | 30 d | Cow K839 after 10 d | 20 d | 30 d |
|---|---|---|---|---|---|---|---|---|
| 12 | 20 × 20 | 18 | 2.01 | 2.10 | 2.04 | 2.53 | 2.29 | 2.21 |
|  |  | 9 | 2.39 | 2.38 | — | 3.08 | 2.66 | — |
|  |  | 7.5 | 2.80 | — | — | 2.59 | — | — |
| 14 | 20 × 20 | 18 | 2.34 | 2.23 | 2.12 | 2.45 | 2.13 | 1.97 |
|  |  | 9 | 3.05 | 2.81 | — | 2.99 | 2.53 | — |
|  |  | 7.5 | 3.32 | — | — | 3.48 | — | — |
| 16 | 20 × 12 (diam) | 8 | 0.39 | 0.31 | — | 0.43 | 0.35 | — |
|  |  | 6 | 0.50 | 0.42 | — | 0.50 | 0.43 | — |
|  |  | 4 | 0.38 | — | — | 0.38 | — | — |

EXAMPLE 5

This Example describes the preparation and testing of cylindrical devices of copper phosphate and copper oxychloride cements, and also devices comprising copper (II) acetate and copper (I) chloride dispersed in copper phosphate cement.

Three sources of copper as base cement-forming component were used:
(i) copper (II) oxide (ex Hopkin & Williams);
(ii) copper (II) oxide calcined at 1200° C.; and
(iii) copper (I) oxide (ex Hopkin & Williams).

Nine sources of acid cement-forming component were used:
(iv) copper (II) chloride (ex Fisons) (saturated aqueous solution);
(ix) 75% w/w aqueous orthophosphoric acid;
(v) 90% w/w aqueous orthophosphoric acid; and
(vi) 100% polyphosphoric acid (ex Aldrich);
(xii) 50% w/w tannic acid;
(xiii) 50% w/w phytic acid;
(xiv) 50% w/w gallic acid;
(xv) 50% w/w mellitic acid;
(xvi) 50% w/w 1,3,5-pentanetricarboxylic acid.

Four sources of copper, dispersible in the cements formed from the above mentioned components by admixture with one or more thereof were used:
(x) copper powder
(vii) copper (I) chloride (ex Fisons)
(xi) copper (II) formate (viii) copper (II) acetate (ex BDH)

The components were mixed together at the ratio shown in Table 5a below and were packed into cylindrical moulds 12 mm×6 mm diameter. These were then sealed for 24–48 hours at 37° C. to form cylindrical devices which were next incorporated in distilled demineralised water and the in vitro release of copper was monitored by atomic absorption spectrophotometry. Results are shown in Table 5b.

EXAMPLE 6

This Example describes the preparation and testing of cylindrical devices of cobalt cements, and also devices comprising cobalt phosphate dispersed in such cements.

Seven sources of base cement-forming component were used:
(i) cobalt (II) carbonate (ex BDH);
(ii) cobalt (II) carbonate heated at 400° C.;

TABLE 5a

| Cement | base component | acid component | ratio | curing temperature (°C.) |
|---|---|---|---|---|
| 17 | (i) + (iii) | (v) | (i):(iii):(v)::1.5 g:0.2 g:1.0 ml | 37 |
| 18 | (i) + (iii) | (v) | (i):(iii):(v)::1.5 g:0.5 g:1.0 ml | 37 |
| 19 | (i) | (vii) + (v) | (i):(vii):(v)::1.5 g:0.5 g:1.0 ml | 37 |
| 20 | (i) | (viii) + (v) | (i):(viii):(v)::1.5 g:0.5 g:1.0 ml | 37 |
| 21 | (i) | (iv) | (i):(iv)::1.5 g:1.0 ml | 37 |
| 22 | (ii) | (vii) + (iv) | (ii):(vii):(iv)::1.5 g:0.5 g:1.0 ml | 37 |
| 23 | (ii) | (vii) + (vi) | (ii):(vii):(vi)::1.5 g:0.5 g:1.0 ml | 37 |
| 24 | (ii) | (v) | (ii):(v)::1.5 g:1.0 ml | 37 |
| 117 | (i) | (v) | (i):(v)::1.27 g:1.0 ml | 37 |
| 118 | (i) | (v) | (i):(v)::1.27 g:1.0 ml | 100 |
| 119 | (i) | (v) | (i):(v)::1.27 g:1.0 ml | 250 |
| 120 | (i)' | (v) | (i)':(v)::0.65 g:1.0 ml | 100 |
| 121 | (i)' | (v) | (i)':(v)::0.65 g:1.0 ml | 250 |
| 122 | (i)' | (v) | (i)':(v)::0.65 g:1.0 ml | 500 |
| 123 | (i) | (v) | (i):(v)::0.96 g:1.0 ml | 37 |
| 124 | (i) | (v) | (i):(v)::0.96 g:1.0 ml | 100 |
| 217 | (i) | (v) | (i):(v)::0.96 g:1.0 ml | 250 |
| 218 | (i) | (ix) | (i):(ix)::1.07 g:1.0 ml | 37 |
| 219 | (i) | (ix) | (i):(ix)::1.5 g:1.0 ml | 37 |
| 220 | (i) | (x) + (v) | (i):(x):(v)::1.5 g:2.5 g:1.0 ml | 37 |
| 221 | (i) | (xi) + (v) | (i):(xi):(v)::1.5 g:0.5 g:1.0 ml | 37 |
| 222 | (ii) | (iv) | (ii):(iv)::1.5 g:1.0 ml | 37 |
| 223 | (i)' | (xii) | (i)':(xii)::1.3 g:1.0 ml | 37 |
| 224 | (i)' | (xiii) | (i)':(xiii)::0.8 g:1.0 ml | 37 |
| 317 | (i)' | (xiv) | (i)':(xiv)::1.0 g:1.0 ml | 37 |
| 318 | (i) | (xv) | (i):(xv)::3.0 g:1.0 ml | 37 |
| 319 | (i) | (xvi) | (i)(xvi)::3.0 g:1.0 ml | 37 |

[(i)' is copper (II) carbonate-derived copper (II) oxide.]

(iii) cobalt (II) acetate (ex BDH);
(iv) cobalt (II) acetate, finely ground;

TABLE 5b

| | Cu leached/day (% w/w of cement) | | | | | | |
|---|---|---|---|---|---|---|---|
| Cement | after 1 day | after 15 days | after 22 days | after 29 days | after 36 days | after 43 days | Comments |
| 17 | 0.21 | 0.26 | 0.12 | 0.008 | 0.003 | — | |
| 18 | 0.14 | 0.20 | 0.065 | 0.004 | 0.004 | — | |
| 19 | 0.47 | 0.42 | 0.042 | 0.019 | 0.002 | — | |
| 20 | 0.53 | 0.20 | 0.052 | 0.005 | 0.002 | — | |
| 21 | 0.039 | 0.019 | 0.030 | 0.036 | 0.032 | 0.040 | releasing 0.041% at day 71 |
| 22 | 0.58 | 0.081 | 0.057 | 0.063 | — | — | |
| 23 | — | 0.0143 | 0.071 | 0.067 | 0.047 | 0.037 | releasing 0.037% at day 57 |
| 24 | 2.02 | 0.453 | 0.157 | 0.044 | — | — | uniform release in vivo |
| 117 | 0.24 | 0.31 | 0.15 | 0.015 | 0.001 | 0.001 | |
| 118 | 1.27 | 0.071 | 0.046 | 0.042 | 0.031 | 0.025 | releasing 0.03% at day 100 |
| 119 | 0.083 | 0.017 | 0.012 | 0.015 | 0.020 | 0.022 | releasing 0.008% at day 85 |
| 120 | 0.34 | 0.15 | 0.010 | 0.011 | 0.006 | 0.006 | |
| 121 | 0.64 | 0.057 | 0.030 | 0.031 | 0.025 | 0.024 | releasing 0.015% at day 92 |
| 122 | 0.14 | 0.019 | 0.015 | 0.016 | 0.013 | 0.009 | |
| 123 | 0.70 | 0.36 | 0.12 | 0.034 | 0.032 | 0.025 | releasing 0.013% at day 50 |
| 124 | 2.25 | 0.074 | 0.052 | 0.064 | 0.062 | 0.045 | |
| 217 | 1.37 | 0.068 | 0.014 | 0.016 | 0.012 | 0.014 | |
| 218 | 0.62 | 0.164 | 0.127 | 0.112 | — | — | |
| 219 | 0.57 | 0.133 | 0.064 | 0.033 | 0.004 | — | |
| 220 | 0.046 | 0.135 | 0.076 | 0.063 | 0.012 | 0.003 | |
| 221 | 1.16 | 0.098 | 0.060 | 0.147 | — | — | |
| 222 | 0.049 | 0.015 | 0.011 | 0.011 | 0.009 | — | |
| 223 | 0.051 | 0.016 | 0.017 | 0.021 | 0.023 | 0.024 | releasing 0.020% at day 120 |
| 224 | 0.156 | 0.015 | 0.011 | 0.009 | 0.010 | 0.012 | releasing 0.009% at day 92 |
| 317 | 0.080 | 0.032 | 0.024 | 0.026 | 0.026 | 0.026 | releasing 0.021% at day 246 |
| 318 | 0.028 | 0.018 | 0.026 | 0.032 | 0.012 | 0.023 | |
| 319 | 0.02 | 0.019 | 0.035 | 0.024 | 0.024 | 0.013 | |

(v) cobalt (II) hydroxide (ex Ventron GmbH) heated at 150° C.;
(vi) cobalt (II) hydroxide heated at 150° C. and loaded with stainless steel (ex Goodfellow Metals) (at ratio 1:2); and
(vii) zinc oxide (ex Fisons).

Thirteen sources of acid cement-forming component were used:
(viii) 90% w/w aqueous orthophosphoric acid;
(ix) 60% w/w aqueous orthophosphoric acid;
(x) 50% w/w aqueous orthophosphoric acid;
(xi) 50% w/w aqueous sodium dihydrogen phosphate (ex Fisons);
(xii) 50% w/w aqueous sodium dihydrogen phosphate comprising 5% w/w cobalt (II) chloride (ex BDH);
(xiii) 50% w/w aqueous cobalt chloride;
(xvi) 50% w/w aqueous zinc chloride;
(xiv) 50% w/w aqueous tannic acid (ex Hopkin & Williams);
(xvii) 50% w/w aqueous L-malic acid;
(xviii) 50% w/w aqueous mellitic acid;
(xix) 50% w/w aqueous 1,3,5-pentanetricarboxylic acid;
(xx) 50% w/w aqueous pyruvic acid;
(xxi) 50% w/w aqueous tartaric acid.

One source of cobalt, dispersible in the cements formed from the above-mentioned components by admixture with one or more thereof, was used:
(xv) cobalt (II) phosphate (ex BDH).

The components were mixed together at the ratio shown in Table 6a below and were packed into cylindrical moulds 12 mm×6 mm diameter. These were then sealed for 24 hours at the curing temperature shown in Table 6a to form cylindrical devices which were next incorporated in distilled demineralized water and the in vitro release of cobalt was monitored by atomic absorption spectrophotometry. Results are shown in Table 6b.

TABLE 6a

| Cement | base component | acid component | ratio | curing temperature (°C.) |
| --- | --- | --- | --- | --- |
| 25 | (i) | (ix) | (i):(ix)::2.0 g:1.0 ml | 37 |
| 26 | (i) | (x) | (i):(x)::2.0 g:1.0 ml | 37 |
| 27 | (i) | (xi) | (i):(xi)::2.5 g:1.0 ml | 37 |
| 28 | (i) | (viii) | (i):(viii)::2.5 g:1.0 ml | 95 |
| 29 | (iii) | (viii) | (iii)(viii)::2.5 g:1.0 ml | 95 |
| 31 | (iv) | (viii) | (iv):(viii)::3.5 g:1.0 ml | 95 |
| 35 | (v) + (xv) | (xi) | (v):(xv):(xi)::1.25 g:0.25 g:1.0 ml | 37 |
| 36 | (vii) | (xiii) | (vii):(xiii)::1.0 g:1.0 ml | 37 |
| 37 | (vi) | (xi) | (vi):(xi)::3.0 g:2.0 ml | 37 |
| 38 | (ii) | (xiv) | (ii):(xiv)::1.5 g:1.0 ml | 37 |
| 39 | (i) | (viii) | (i):(viii)::2.5 g:1.0 ml | 37 |
| 40 | (iv) | (ix) | (iv):(ix)::2.0 g:1.0 ml | 37 |
| 125 | (v) | (x) | (v):(x)::2.5 g:1.0 ml | 37 |
| 126 | (v) | (xi) | (v):(xi)::1.25 g:1.0 ml | 37 |
| 127 | (i) | (xvi) | (i):(xvi)::2.0 g:1.0 ml | 37 |
| 128 | (v) | (xvii) | (i):(xvii)::2.0 g:1.0 ml | 37 |
| 129 | (v) | (xviii) | (v):(xviii)::1.8 g:1.0 ml | 37 |
| 130 | (v) | (xix) | (v):(xix)::2.0 g:1.0 ml | 37 |
| 131 | (v) | (xx) | (v):(xx)::2.0 g:1.0 ml | 95 |
| 132 | (v) | (xxi) | (v):(xxi)::2.0 g:1.0 ml | 37 |
| 133 | (v) | (xiv) | (v):(xiv)::2.0 g:1.0 ml | 37 |

TABLE 6b

| | Co leached/day (% w/w of cement) | | | | | | |
| --- | --- | --- | --- | --- | --- | --- | --- |
| Cement | after 1 day | after 15 days | after 22 days | after 29 days | after 36 days | after day 43 | Comments |
| 25 | 0.012 | 0.031 | 0.036 | 0.036 | 0.036 | 0.038 | releasing 0.038% at day 150 |
| 26 | 0.003 | 0.010 | 0.014 | 0.020 | 0.015 | 0.015 | releasing 0.015% at day 190 |
| 27 | 0.004 | 0.010 | 0.018 | 0.017 | 0.019 | 0.024 | releasing 0.024% at day 190 |
| 28 | 0.30 | 0.065 | 0.065 | 0.064 | 0.063 | 0.067 | releasing 0.036% at day 148 |
| 29 | 6.7 | 0.033 | 0.021 | 0.031 | 0.020 | 0.024 | releasing 0.020% at day 148 |
| 31 | 1.45 | 0.123 | 0.106 | 0.056 | 0.036 | 0.028 | releasing 0.028% at day 85 |
| 35 | 0.006 | 0.028 | 0.019 | 0.026 | 0.023 | 0.028 | releasing 0.028% at day 50 |
| 36 | 0.34 | 0.076 | 0.050 | 0.054 | 0.021 | 0.047 | releasing 0.036% at day 50 |
| 37 | 0.0007 | 0.014 | 0.017 | 0.025 | 0.028 | — | |
| 38 | 0.071 | 0.036 | 0.028 | 0.030 | 0.032 | 0.035 | releasing 0.020% at day 148 |
| 39 | 0.48 | 0.048 | 0.047 | 0.067 | 0.038 | 0.035 | |
| 40 | 1.00 | 0.049 | 0.037 | 0.029 | 0.028 | 0.018 | releasing 0.010% at day 99 |
| 125 | — | 0.025 | 0.016 | 0.015 | 0.013 | 0.008 | |
| 126 | 0.011 | 0.025 | 0.024 | 0.024 | 0.030 | 0.025 | releasing 0.031% at day 57 |
| 127 | 4.81 | 0.027 | 0.016 | — | 0.017 | 0.016 | releasing 0.018% at day 50 |
| 128 | 0.875 | 0.30 | 0.168 | 0.133 | 0.130 | 0.065 | |
| 129 | 0.062 | 0.015 | 0.012 | 0.011 | 0.002 | 0.006 | |
| 130 | 0.485 | 0.203 | 0.136 | 0.118 | — | — | |
| 131 | 1.44 | 0.139 | 0.049 | 0.043 | 0.047 | 0.032 | |
| 132 | 0.227 | 0.081 | 0.065 | 0.070 | 0.077 | 0.061 | |
| 133 | 0.195 | 0.084 | 0.051 | 0.057 | 0.054 | 0.041 | releasing 0.052% at day 57 |

EXAMPLE 7

This Example describes the preparation and testing of cylindrical devices of copper-cobalt cements, and also devices comprising cobalt phosphate cement dispersed in copper phosphate cements.

Two sources of base cement-forming component were used:

(i) copper (II) oxide; and
(ii) cobalt (II) hydroxide heated at 150° C.

Six sources of acid cement-forming component were used:
(iii) 90% w/w aqueous orthophosphoric acid;
(iv) 90% w/w aqueous orthophosphoric acid comprising 5% w/w cobalt phosphate;
(v) 50% aqueous cobalt (II) chloride;
(vi) saturated aqueous cobalt (II) chloride;
(vii) saturated aqueous copper (II) chloride; and
(viii) 75% w/w aqueous orthophosphoric acid comprising 6% cobalt (II) orthophosphate.

One source of cobalt, dispersible in the cements formed from the above mentioned components by admixture with one or more thereof, was used:
(ix) cobalt phosphate cement (from cobalt (II) hydroxide and 60% orthophosphoric acid at a p:1::1:1 g/ml); and
(x) cobalt (II) phosphate.

The components were mixed together at the ratio shown in Table 7a below and were packed into cylindrical moulds 12 mm×6 mm diameter. These were then sealed for 36 hours at the curing temperature shown to form cylindrical devices. The devices were next incorporated in distilled demineralized water and in vitro release of cobalt was monitored by atomic absorption spectrophotometry.

Results are shown in Table 7b.

One source of base cement-forming component was used which was
(i) copper (II) oxide;

Four sources of acid cement-forming component were used:
(ii) 90% w/w aqueous orthophosphoric acid;
(iii) saturated aqueous copper (II) chloride;
(iv) 90% w/w aqueous orthophosphoric acid comprising 5% w/w zinc selenite; and
(v) 90% w/w aqueous orthophosphoric acid comprising 5% w/w copper (II) selenite;
(viii) 90% w/w aqueous orthophosphoric acid comprising 5% w/w calcium selenite;
(ix) 90% w/w aqeous orthophosphoric acid comprising 5% w/w calcium selenate.

Two sources of solid selenites, dispersible in the cement formed from the above mentioned components by admixture with one or more thereof, were used:
(vi) copper (II) selenite (ex BDH); and
(vii) zinc selenite (ex Fluka).

The components were mixed together at the ratio shown in Table 8a below and were packed into cylindrical moulds 12 mm×6 mm diameter. These were then sealed for 36 hours at the curing temperature shown to form cylindrical devices. The devices were incorporated in distilled demineralized water and the in vitro release of selenium was monitored by heated graphite furnace atomic absorption spectrophotometry.

TABLE 7a

| Cement | base component | acid component | ratio | curing temperature (°C.) |
|---|---|---|---|---|
| 41 | (i) | (vi) | (i):(vi)::1.75 g:1 ml | 37 |
| 42 | (ii) | (vii) | (ii):(vii)::2 g:1 ml | 37 |
| 43 | (i) + (x) | (iii) | (i):(x):(iii)::1.2 g:0.2 g:1 ml | 37 |
| 44 | (i) | (v) | (i):(v)::1.5 g:1 ml | 37 |
| 45 | (i) | (viii) | (i):(viii)::2 g:1 ml | 37 |
| 46 | (i) + (ix) | (iii) | (i):(ix):(iii)::1.0 g:0.2 g:1 ml | 37 |
| 47 | (i) + (x) | (iii) | (i):(x):(iii)::1.2 g:0.05 g:1 ml | 37 |
| 48 | (i) + (ix) | (iii) | (i):(ix):(iii)::1.0 g:0.5 g:1 ml | 37 |
| 49 | (i) | (iv) | (i):(iv)::1.2 g:1 ml | 37 |
| 50 | (i) | (viii) | (i):(viii)::1.5 g:1 ml | 37 |

TABLE 7b

| | Cu and Co leached/day (% w/w of cement) | | | | | | | | | | | |
| | after 1 day | | after 15 days | | after 22 days | | after 29 days | | after 36 days | | after 43 days | |
| Cement | Cu | Co | Cu | Co | Cu | Co | Cu | Co | Cu | Co | Cu | Co | Comments |
|---|---|---|---|---|---|---|---|---|---|---|---|---|---|
| 41 | 0.005 | 0.094 | 0.005 | 0.041 | 0.020 | 0.037 | | | | | | | |
| 42 | 0.004 | 0.52 | 0.002 | 0.022 | | | | | | | | | |
| 43 | 1.43 | 0.49 | 0.27 | 0.042 | 0.182 | 0.016 | 0.037 | 0.002 | | | | | |
| 44 | 0.016 | 0.12 | 0.012 | 0.021 | 0.017 | 0.022 | 0.028 | 0.022 | 0.043 | 0.027 | 0.036 | 0.023 | reasonable Co release rate |
| 45 | 0.070 | 0.042 | 0.080 | 0.041 | 0.002 | | | | | | | | |
| 46 | 2.13 | 0.64 | 0.059 | 0.018 | 0.090 | 0.024 | 0.168 | 0.037 | 0.128 | 0.022 | 0.081 | 0.018 | |
| 47 | 1.19 | 0.042 | 0.40 | 0.016 | 0.26 | 0.007 | 0.003 | 0 | | | | | |
| 48 | 0.99 | 1.03 | 0.026 | 0.020 | 0.056 | 0.025 | 0.107 | 0.031 | | | | | |
| 49 | 1.02 | 0.071 | 0.29 | 0.011 | 0.25 | 0.005 | 0.031 | 0 | | | | | |
| 50 | 0.42 | 0.256 | 0.028 | 0.006 | | | | | | | | | |

EXAMPLE 8

This Example describes the preparation and testing of cylindrical devices of copper comprising selenites dispersed therein.

Results are shown in Table 8b.

TABLE 8a

| Cement | base component | acid component | ratio | curing temperature (°C.) |
|---|---|---|---|---|
| 51 | (i) + (vi) | (ii) | (i):(vi):(ii)::1.2 g:0.05 g:1 ml | 37 |
| 52 | (i) + (vi) | (ii) | (i):(vi):(ii)::1.2 g:0.2 g:1 ml | 37 |
| 54 | (i) + (vii) | (iii) | (i):(vii):(iii)::1.5 g:0.1 g:1 ml | 37 |

TABLE 8a-continued

| Cement | base component | acid component | ratio | curing temperature (°C.) |
|---|---|---|---|---|
| 55 | (i) + (vi) | (iii) | (i):(vi):(iii)::1.5 g:0.1 g:1 ml | 37 |
| 56 | (i) | (iv) | (i):(iv)::2 g:1 ml | 37 |
| 57 | (i) | (v) | (i):(v)::2 g:1 ml | 37 |
| 58 | (i) + (vi) | (iii) | (i):(vi):(iii)::1.5 g:0.2 g:1 ml | 37 |
| 59 | (i) + (vii) | (iii) | (i):(vii):(iii)::1.5 g:0.2 g:1 ml | 37 |
| 62 | (i) + (vi) | (ii) | (i):(vi):(ii)::4 g:1 g:1 ml | 37 |
| 63 | (i) + (vi) | (ii) | (i):(vi):(ii)::2 g:0.2 g:1 ml | 37 |
| 151 | (i) | (viii) | (i):(viii)::1 g:1 ml | 37 |
| 152 | (i) | (ix) | (i):(ix)::1 g:1 ml | 37 |
| 153 | (i) | (iv) | (i):(iv)::1 g:1 ml | 37 |
| 154 | (i) + (vii) | (ii) | (i):(vii):(ii)::1.2 g:0.2 g:1 ml | 37 |
| 155 | (i) + (vi) | (ii) | (i):(vi):(ii)::2 g:0.2 g:1 ml | 37 |

TABLE 8b

| | Cu and Se leached/day (% w/w of cement) | | | | | | | | | |
|---|---|---|---|---|---|---|---|---|---|---|
| | after 15 days | | after 22 days | | after 29 days | | after 36 days | | after 43 days | |
| Cement | Cu | Se | Cu | Se | Cu | Se | Cu | Se | Cu | Se | Comments |
| 51 | 0.29 | 0.007 | 0.23 | 0.007 | 0.21 | 0.005 | | | | | |
| 52 | 0.082 | 0.011 | 0.24 | 0.026 | 0.23 | 0.021 | | | | | |
| 54 | 0.018 | 0.006 | 0.011 | 0.006 | 0.007 | 0.006 | 0.006 | 0.005 | | | |
| 55 | 0.016 | 0.002 | 0.015 | 0.002 | 0.014 | | | 0.010 | 0.012 | 0.003 | |
| 56 | 0.22 | 0.007 | 0.15 | 0.007 | 0.062 | 0.003 | | | | | |
| 57 | 0.23 | 0.010 | 0.15 | 0.005 | 0.071 | 0.004 | | | | | |
| 58 | | 0.001 | | 0.001 | | | | | 0.008 | 0.001 | |
| 59 | 0.014 | 0.003 | 0.010 | 0.003 | | | | | 0.007 | 0.005 | |
| 62 | | 0.004 | 0.003 | 0.001 | | | | | | | |
| 63 | 0.15 | 0.012 | 0.062 | 0.012 | | | | | | | |
| 151 | 0.30 | 0.016 | 0.19 | 0.009 | 0.146 | — | 0.170 | 0.006 | | | |
| 152 | 0.43 | 0.012 | 0.28 | | | | | | | | |
| 153 | 0.46 | 0.016 | 0.29 | 0.009 | | | | | | | |
| 154 | 0.42 | 0.042 | 0.30 | 0.063 | 0.39 | 0.062 | | | | | more stable; higher Se release |
| 155 | 0.32 | 0.026 | 0.20 | 0.023 | 0.19 | 0.028 | | | | | stable Se release |

EXAMPLE 9

This Example describes the preparation and testing of cylindrical devices of, in the main, oxyhalide and oxychalocogenate cements.

Six sources of base cement-forming component were used:
(i) zinc oxide;
(ii) cobalt (II) hydroxide;
(iii) cobalt (II) carbonate;
(iv) copper (II) oxide, finely ground;
(v) copper (II) oxide, calcined at 1200° C.;

The following other cement-forming components were used:
(vi) saturated (60% w/w) zinc sulphate aqueous solution;
(vii) saturated (50% w/w) zinc iodide aqueous solution;
(viii) saturated (65% w/w) cobalt (II) sulphate aqueous solution;
(ix) saturated (50% w/w) cobalt (II) iodide aqueous solution;
(x) saturated (65% w/w) copper (II) sulphate aqueous solution;
(xi) 90% w/w aqueous orthophosphoric acid;
(xii) copper (II) iodate;
(xiii) saturated (75% w/w) copper (II) chloride aqueous solution;
(xiv) saturated (50% w/w) zinc chloride aqueous solution.

The components were mixed together at the ratio shown in Table 9a below and were packed into cylindrical moulds 12 mm×6 mm diameter. These were then sealed for 36 hours at the curing temperature shown to form cylindrical devices. The devices were incorporated in distilled demineralized water and the in vitro release of cobalt, copper, zinc and iodine was monitored by atomic absorption spectrophotometry.

Results are shown in Table 9b.

TABLE 9a

| Cement | base component | acid component | ratio | curing temperature (°C.) |
|---|---|---|---|---|
| 65 | (i) | (viii) | (i):(viii)::2 g:1 ml | 37 |
| 66 | (ii) | (iv) | (ii):(iv)::2.4 g:1 ml | 37 |
| 67 | (i) | (ix) | (i):(ix)::1.0 g:1 ml | 37 |
| 68 | (ii) | (vii) | (ii):(vii)::1.0 g:1 ml | 37 |
| 69 | (iii) | (vii) | (iii):(vii)::1.0 g:1 ml | 37 |
| 70 | (i) | (x) | (i):(x)::2.2 g:1 ml | 37 |
| 71 | (iv) | (vi) | (iv):(vi)::4.0 g:1 ml | 37 |
| 72 | (iv) | (xii) + (xi) | (iv):(xi):(xii):1.5 g:1 ml:0.5 g | 37 |
| 73 | (v) | (vii) | (v):(vii)::1 g:1 ml | 37 |
| 74 | (i) | (ix) | (i):(ix)::1 g:1 ml | 37 |
| 75 | (i) | (xiii) | (i):(xiii)::1 g:1 ml | 37 |
| 76 | (ii) | (xiv) | (ii):(xiv)::2 g:1 ml | 37 |

TABLE 9b

| Cement | \multicolumn{12}{c}{Trace elements leached/day (% w/w of element)} |
|---|---|---|---|---|---|---|---|---|---|---|---|---|
| | after 1 day | | after 15 days | | after 22 days | | after 29 days | | after 36 days | | after 43 days | |
| | Zn | Co | Zn | Co | Zn | Co | Zn | Co | Zn | Co | Zn | Co |
| 65 | 0.034 | 0.086 | 0.022 | 0.053 | 0.015 | 0.035 | 0.015 | 0.028 | 0.015 | 0.023 | 0.010 | 0.019 |
| 66 | 0.013 | 2.47 | 0.011 | 0.017 | 0.002 | 0.011 | 0.002 | 0.015 | 0.001 | 0.011 | 0.001 | 0.009 |
| 67 | 1.54 | 2.18 | 0.011 | 0.019 | 0.038 | 0.010 | | | | | | |
| 68 | 0.025 | 2.31 | 0.090 | 0.050 | 0.007 | 0.026 | 0.006 | 0.021 | 0.005 | 0.019 | 0.004 | 0.015 |
| 69 | 1.16 | 2.03 | 0.011 | 0 | 0.010 | 0 | 0.012 | 0 | 0.013 | 0 | 0.003 | 0.020 |
| | Zn | Cu | Zn | Cu | Zn | Cu | Zn | Cu | Zn | Cu | Zn | Cu |
| 70 | 0.094 | 0.003 | 0.026 | 0 | 0.018 | 0 | 0.017 | 0 | 0.013 | 0 | 0.012 | 0 |
| 71 | 0.153 | 0.008 | 0.031 | 0.007 | 0.020 | 0.011 | | | | | | |
| | Cu | I | Cu | I | Cu | I | Cu | I | Cu | I | Cu | I |
| 72 | 0.184 | | 0.116 | 0.120 | 0.120 | 0.064 | 0.118 | 0.056 | 0.069 | | | |
| 73 | 0.048 | | 0.012 | | 0.020 | | 0.015 | | 0.012 | | | |
| | Co | I | Co | I | Co | I | Co | I | Co | I | Co | I |
| 74 | 2.18 | | 0.019 | 0.105 | 0.010 | 0.060 | | 0.050 | | | | |
| | Cu | Zn | Cu | Zn | Cu | Zn | Cu | Zn | Cu | Zn | Cu | Zn |
| 75 | 0.004 | 1.19 | 0.004 | 0.053 | 0.005 | 0.092 | 0.005 | 0.066 | 0.005 | 0.040 | 0.006 | 0.025 |
| | Co | Zn | Co | Zn | Co | Zn | Co | Zn | Co | Zn | Co | Zn |
| 76 | 1.36 | 0.086 | 0.055 | 0.021 | 0.038 | 0.012 | 0.023 | 0.011 | 0.018 | 0.009 | 0.019 | 0.009 |

EXAMPLE 10

This Example describes the preparation and testing of cylindrical devices of a copper phosphate cement comprising nicotinamide.

The components were mixed together in the ratio 1.3 g CuO:1.0 ml of 90% phosphoric acid: and 0.2 g nicotinamide; and were then packed into cylindrical moulds 12 mm×6 mm diameter. These were then sealed for 36 hours at 37° C.

The devices were next incorporated in distilled demineralised water and the in vitro release of the nicotinamide was monitored by UV absorption spectrophotometry.

The results are shown in Table 10.

TABLE 10

| Time (days) | % nicotinamide released |
|---|---|
| 1 | 17.6 |
| 2 | 25.5 |
| 3 | 31.4 |
| 6 | 43.0 |
| 7 | 45.9 |
| 8 | 49.0 |
| 9 | 52.1 |
| 10 | 55.3 |
| 13 | 64.6 |
| 15 | 67.1 |

EXAMPLE 11

Proceeding in essentially the same manner as in Examples 5 to 9 a variety of cement were prepared; their compositions, preparation and release rates are shown in the following Tables 11 to 13 inclusive.

TABLE 11

| Cement | Ratio of components | Day 16 Cu | Day 16 Zn/Mg | Day 16 Se | Day 22 Cu | Day 22 Zn/Mg | Day 22 Se | Day 29 Cu | Day 29 Zn/Mg | Day 29 Se | Day 36 Cu | Day 36 Zn/Mg | Day 36 Se | Day 43 Cu | Day 43 Zn/Mg | Day 43 Se |
|---|---|---|---|---|---|---|---|---|---|---|---|---|---|---|---|---|
| CuO(fine) + 50% Gallic Acid + ZnSeO$_3$ | 3 g:1 ml:0.5 g | 0.004 | 0.015 | 0.03 | 0.004 | 0.020 | 0.024 | 0.005 | 0.014 | 0.023 | 0.005 | 0.013 | 0.0257 | 0.003 | 0.0105 | 0.022 |
| CuO(fine) + 50% Mellitic acid + ZnSeO$_3$ | 3 g:1 ml:0.5 g | 0.013 | 0.012 | 0.03 | 0.009 | 0.014 | 0.026 | 0.011 | 0.009 | 0.026 | 0.008 | 0.008 | 0.016 | 0.009 | 0.007 | 0.014 |
| CuO(fine) + 50% Phytic Acid + ZnSeO$_3$ | 3 g:1 ml:0.5 g | 0.0027 | 0.0029 | 0.015 | 0.002 | 0.005 | 0.011 | 0.003 | 0.002 | 0.008 | 0.001 | 0.002 | 0.012 | 0.0007 | 0.002 | 0.008 |
| CuO(fine) + 50% Pentan (COOH)$_3$ + ZnSeO$_3$ | 3 g:1 ml:0.5 g | 0.019 | 0.014 | 0.023 | 0.016 | 0.019 | 0.021 | 0.014 | 0.011 | 0.023 | 0.007 | 0.009 | 0.014 | 0.009 | 0.008 | 0.011 |
| CuO(fine) + 50% Tannic Acid + ZnSeO$_3$ | 3 g:1 ml:0.5 g | 0.001 | 0.008 | 0.015 | 0.002 | 0.009 | 0.010 | 0.001 | 0.007 | 0.011 | 0.002 | 0.006 | 0.013 | 0.004 | 0.006 | 0.006 |
| MgO + CuSeO$_4$ (satd.(25%)) | 1.2 g:1 ml | 0 | 0.055 | 0.093 | 0 | 0.036 | 0.069 | 0 | 0.029 | 0.041 | 0 | 0.028 | 0.035 | 0 | 0.026 | 0.026 |
| ZnO + CuSeO$_4$ (satd.(25%)) | 2 g:1 ml | 0 | 0.035 | 0.018 | 0 | 0.019 | 0.015 | 0.012 | 0 | 0.011 | 0.012 | 0 | 0.012 | 0.010 | — | — |
| CuO + ZnSeO$_4$ (satd.(50%)) | 4 g:1 ml | 0.007 | 0.027 | 0.046 | 0.015 | 0.005 | 0.062 | — | — | — | — | — | — | — | — | — |
| CuO + 90% H$_3$PO$_4$ + BaSeO$_4$ (fine) | 3 g:1 ml:1 g | — | — | — | 0.004 | — | 0.023 | 0.002 | — | 0.021 | 0.001 | — | 0.020 | 0.002 | — | 0.018 |
| CuO + 90% H$_3$PO$_4$ (95° C.) + ZnSeO$_3$ | 1.2:1 ml:0.4 g | 0.013 | — | 0.026 | 0.012 | — | 0.022 | 0.053 | — | — | — | — | — | — | — | — |
| CuO + 90% H$_3$PO$_4$ (fine) + ZnSeO$_3$ (95° C.) | 1.2:1 ml:0.2 g | 0.105 | — | 0.037 | 0.057 | — | 0.021 | 0.041 | — | — | — | — | — | — | — | — |

TABLE 12

| Cement | Ratio of components | Temp. of cure | Day 16 Co | Day 16 Zn/Mg | Day 16 Se | Day 22 Co | Day 22 Zn/Mg | Day 22 Se | Day 29 Co | Day 29 Zn/Mg | Day 29 Se | Day 36 Co | Day 36 Zn/Mg | Day 36 Se | Day 43 Co | Day 43 Zn/Mg | Day 43 Se |
|---|---|---|---|---|---|---|---|---|---|---|---|---|---|---|---|---|---|
| $Co(OH)_2$ + 50% Malic Acid + $ZnSeO_3$ | 2 g:1 ml:0.2 g | 37° | 0.135 | 0.003 | 0.017 | 0.127 | 0.003 | 0.012 | 0.078 | 0.002 | 0.007 | 0.057 | 0.002 | 0.006 | 0.033 | 0 | 0.005 |
| $Co(OH)_2$ + 50% Mellitic Acid + $ZnSeO_3$ | 1.6:1 ml:0.2 g | 37° | — | — | 0.004 | *0.001 | 0 | — | 0.006 | 0 | — | — | — | — | — | — | — |
| $Co(OH)_2$ + 50% Pentan(COOH)$_3$ + $ZnSeO_3$ | 2 g:1 ml:0.2 g | 37° | — | — | 0.003 | 0.101 | 0 | — | 0.07 | 0 | — | — | — | — | — | — | — |
| $Co(OH)_2$ + 50% Pyruvic Acid + $ZnSeO_3$ | 2 g:1 ml:0.2 g | 37° | 0.053 | 0.002 | 0.013 | 0.05 | 0.002 | 0.009 | 0.038 | 0.001 | 0.014 | 0.043 | 0.001 | 0.014 | 0.036 | 0.001 | 0.012 |
| $Co(OH)_2$ + 50% m-Tartaric Acid + $ZnSeO_3$ | 2 g:1 ml:0.2 g | 37° | 0.201 | 0.016 | 0.028 | 0.21 | 0.015 | 0.018 | 0.116 | 0.007 | 0.026 | 0.144 | 0.009 | 0.028 | 0.097 | 0.006 | 0.016 |
| $Co(OH)_2$ + 50% Tannic Acid + $ZnSeO_3$ | 2 g:1 ml:0.2 g | 37° | 0.061 | 0.004 | 0.027 | 0.047 | 0.004 | 0.021 | 0.040 | 0.003 | 0.020 | 0.048 | 0.003 | 0.017 | 0.038 | 0.023 | 0.024 |
| $Co(OH)_2$ + $CoSeO_4$ (A) | 2 g:1 ml | 95° | 0.069 | — | 0.103 | 0.067 | — | 0.114 | 0.056 | — | 0.085 | 0.043 | — | 0.062 | 0.041 | — | 0.052 |
| MgO + $CoSeO_4$ (A) | 1.3 g:1 ml | 37° | 0.016 | 0.049 | 0.114 | 0 | 0.031 | 0.104 | 0 | 0.031 | 0.070 | 0 | 0.025 | 0.058 | 0 | 0.026 | 0.052 |
| ZnO + $CoSeO_4$ (A) | 2 g:1 ml | 37° | 0.017 | 0.016 | 0.046 | 0.014 | 0.014 | 0.045 | 0.012 | 0.090 | 0.03 | 0.007 | 0.086 | 0.027 | 0.010 | 0.010 | 0.028 |
| $Co(OH)_2$ + $ZnSeO_4$ (A) | 2.4 g:1 ml | 37° | 0.022 | 0.0017 | 0.023 | 0.013 | 0.0001 | 0.02 | 0.010 | 0 | 0.012 | 0.007 | 0.001 | 0.013 | 0.007 | 0 | 0.009 |

A = 50% solutions

TABLE 13

Trace elements leached/day (% w/w of cement)

| Cement | Ratio of components | Temp of cure | Day 16 | | | Day 22 | | | Day 29 | | |
|---|---|---|---|---|---|---|---|---|---|---|---|
| | | | Mg | Zn | Se | Mg | Zn | Se | Mg | Zn | Se |
| $MgO + MgSeO_4$ (A) | 1:2 g:1 ml | 37° | — | | 0.0988 | 0.059 | — | 0.119 | 0.050 | — | 0.114 |
| $MgO + ZnSeO_4$ (A) | 1.0 g:1 ml | 37° | — | 0 | 0.110 | 0.031 | 0.0004 | 0.115 | 0.034 | 0 | 0.083 |
| $ZnO + ZnSeO_4$ (A) | 2.0 g:1 ml | 37° | — | 0.0 | 0.053 | — | 0.031 | 0.056 | — | 0.025 | 0.046 |

| | | | Cu | Co | Se | Cu | Co | Se | Cu | Co | Se |
|---|---|---|---|---|---|---|---|---|---|---|---|
| $Co(OH)_2 + CuSeO_4$ (B) | 2.0 g:1 ml | 37° | 0 | 0.029 | 0.013 | 0 | 0.025 | 0.006 | 0 | 0.017 | 0.004 |

| | | | Day 36 | | | Day 43 | | |
|---|---|---|---|---|---|---|---|---|
| | | | Mg | Zn | Se | Mg | Zn | Se |
| $MgO + MgSeO_4$ (A) | 1:2 g:1 ml | 37° | 0.051 | — | 0.096 | 0.054 | — | 0.098 |
| $MgO + ZnSeO_4$ (A) | 1.0 g:1 ml | 37° | 0.029 | 0 | 0.074 | 0.030 | 0 | 0.067 |
| $ZnO + ZnSeO_4$ (A) | 2.0 g:1 ml | 37° | — | 0.021 | 0.041 | — | 0.021 | 0.040 |

| | | | Cu | Co | Se | Cu | Co | Se |
|---|---|---|---|---|---|---|---|---|
| $Co(OH)_2 + CuSeO_4$ (B) | 2.0 g:1 ml | 37° | 0 | 0.020 | | 0 | 0.024 | 0.002 |

| Cement | Ratio of components | Temp of cure | Day 16 | | | | Day 22 | | | |
|---|---|---|---|---|---|---|---|---|---|---|
| | | | Cu | Co | Zn | Se | Cu | Co | Zn | Se |
| CuO(fine) + $Co_3(PO_4)_2$ + $ZnSeO_3$ + 90% $H_3PO_4$ | 1.2 g: 0.2 g: 0.2 g:1 ml | 95° | 0.138 | 0.195 | 0.03 | 0.04 | 0.099 | 0.044 | 0.026 | 0.033 |

| | | | Day 29 | | | | Day 36 | | | |
|---|---|---|---|---|---|---|---|---|---|---|
| | | | Cu | Co | Zn | Se | Cu | Co | Zn | Se |
| CuO(fine) + $Co_3(PO_4)_2$ + $ZnSeO_3$ + 90% $H_3PO_4$ | 1.2 g: 0.2 g: 0.2 g:1 ml | 95° | 0.091 | 0.033 | 0.023 | 0.033 | 0.062 | 0.018 | 0.013 | 0.019 |

A = 50% solutions
B = 25% solutions

EXAMPLE 12

Fourteen cylindrical devices (20 mm×12 mm) of cement 117, mean weight 4.78 g (ranging from 4.60 g to 5.25 g), were provided. Two devices were dissolved in hydrochloric acid for analysis of initial copper content (by atomic absorption spectrophotometry) and the remainder were placed, in groups of four devices, into three polypropylene mesh bags which were then inserted into the reticulum of a cow having a fistulated rumen. The devices were removed at regular intervals, weighed, and replaced save that, at each such weighing, one device was dissolved in hydrochloric acid for analysis of the remaining copper content.

Over the 72 day period of the experiment the mean weight of the devices was found to decrease approximately linearly by 0.26%/day (ranging from 0.18 to 0.38%/day), although extrapolation to zero time suggests an initial weight increase of approximately 3%. The copper content of the devices was found to decrease from an initial 33.8% to a mean of 32.7% by weight (ranging from 30.7 to 35.0%). All of the devices maintained their cylindrical geometry in vivo.

EXAMPLE 13

Ten cylindrical devices (20 mm×12 mm) of cement 119, mean weight 4.35 g, were treated in essentially the same manner as in Example 12. The mean weight of the devices was found to decrease approximately linearly by 0.4%/day with an initial weight increase of approximately 15%. The copper content of the devices was found to decrease from an initial 37.7% to a mean of 32.8% by weight. The geometry of the devices became irregular in vivo.

EXAMPLE 14

Fourteen cylindrical devices (20 mm×12 mm) of cement 118, mean weight 8.9 g, comprising 50% by weight of stainless steel as filler were provided. These were treated in essentially the same manner as those of Example 12. Apart from a 14 day period (days 14 to 28) (in which the host cow had a jaw infection and was not eating), the devices lost weight at an approximately linear rate of 7 mg/day (2.3 mg Cu/day). After day 70 the rate increased to 9.5 mg/day (3.2 mg Cu/day).

EXAMPLE 15

Twenty cylindrical devices (18 mm×45 mm) of cement 117 comprising 50% by weight stainless steel as filler, mean weight 39.9 g, were provided. One was retained for analysis of initial copper content and the remainder were given, one each, by mouth to 19 sheep. The sheep were then X-rayed; and it was confirmed that each device resided in the host's reticulum. Four sheep were slaughtered after 1 month, 5 after 2 months, 5 after 4 months and the last 5 were slaughtered after 6 months.

The devices were recovered at slaughter, as was each host liver, and both were analysed for copper content. Results are shown in Table 14.

TABLE 14

| Months in reticulum | Mean wt. devices (g) | | Mean Cu content of device (g) | Liver Cu content (ppm.wet wt) | |
|---|---|---|---|---|---|
| | wet | desiccated | | mean | range |
| 0 | 39.9 | | | | |
| 1 | 39.6 | 37.0 | 5.38 | 97 | 47–174 |
| 2 | 39.6 | 36.8 | 5.61 | 93 | 50–148 |
| 4 | 38.7 | 36.4 | 5.64 | 114 | 59–151 |
| 6 | 39.6 | 37.0 | 5.54 | 182 | 127–287 |

All of the devices retained their geometry in vivo but were coated in a thin layer of black material. All remained in the reticular of the respective hosts.

EXAMPLE 16

Eight cylindrical devices (20 mm×20 mm) of cement 47, mean weight 13.58 g, were provided. Two devices were analysed for initial copper and cobalt content in essentially the same manner as in Example 12 and the remainder were placed in the reticulum of a cow having a fistulated rumen. The devices were weighted at intervals for 64 days. Analytical results were shown in Table 15.

TABLE 15

|  | Cu | Co |
|---|---|---|
| Initial content (%) | 33.5 | 0.60 |
| After 64 days in reticulum |  |  |
| (% initial weight) | 31.8 | 0.44 |
| % dissolved | 5 | 27 |
| g released | 0.22 | 0.22 |

The results suggest that this cement has limited solubility in vivo.

EXAMPLE 17

Six cylindrical devices (20×20 mm) of cement 43, mean weight approximately 14 g, were provided. Two devices (A and B) were analysed for initial copper and cobalt content and the remainder were placed in the reticulum of a cow having a fistulated rumen. Two devices (1 and 2) were removed for analysis after 21 days and the last two (3 and 4) after 41 days. Analytical results are shown in Table 16.

TABLE 16

Copper and cobalt contents of devices after incubation in reticulum.

| Device | Initial wt. (g) | Days in reticulum | Weight change | Cu (g) | Original Cu (g) | Cu loss (g) | Co (mg) | Original Co (mg) | Co loss (mg) |
|---|---|---|---|---|---|---|---|---|---|
| A | 13.772 | 0 | 0 | 2.51 | 2.51 |  | 351 | 351 |  |
| B | 13.720 | 0 | 0 | 2.34 | 2.34 |  | 350 | 350 |  |
| 1 | 13.920 | 21 | +0.812 | 2.23 | 2.45 | 0.22 | 332 | 355 | 23 |
| 2 | 13.593 | 21 | +0.639 | 2.21 | 2.39 | 0.18 | 328 | 347 | 19 |
| 3 | 14.127 | 41 | +0.243 | 2.07 | 2.49 | 0.42 | 328 | 360 | 32 |
| 4 | 14.248 | 41 | +0.165 | 2.08 | 2.51 | 0.43 | 324 | 363 | 39 |

It will be seen from Table 16 that although the devices have not lost weight nonetheless they have been releasing copper and cobalt at an approximate rate, respectively, of 10 mg Cu/day and 0.9 mg Co/day.

EXAMPLE 18

Eighteen cylindrical devices essentially the same as those of Example 17 were provided. Six devices were analysed for initial copper and cobalt content and the remainder were given, one each, by mouth to 12 three month old Finn×Dorset sheep. Ten similar sheep were used as control animals. All the sheep grazed pasture until their slaughter between 98 and 133 days after administration of the device. Blood samples were taken for Cu analysis before dosing and at slaughter. All the devices and the livers were recovered at slaughter and analysed for Cu content.

The mean content of original devices was 36.7% Cu and 2.2% Co. There were no significant differences in the weight of the pellets resulting from incubation in the reticula but the Cu and Co content decreased resulting in an average loss of 3.9 mg Cu/ (ranging from 1.7 mg to 8.2 mg Cu/ and 0.32 mg Co/ (ranging from 0.05 to 0.67 mg Co/) day.

These rates are similar to those determined in the cow in Example 17. No significant differences could be detected between treated and untreated sheep with respect to blood or liver copper concentration; but none of the sheep could be considered to be copper deficient.

EXAMPLE 19

Eight cylindrical devices (20 mm×20 mm) of cement 154 were provided. Two devices were analysed for initial copper content while the remainder were placed in the reticulum of a cow having a fistulated rumen. Two devices were removed for analysis after 28 days, 2 after 56 days and 2 after 87 days.

Weight changes were erratic. When the devices were analysed those which had not been in the reticulum were completely soluble but an insoluble orange-red residue, which increased in amount with incubation time in the reticulum, formed within the remainder.

Copper analyses (duplicate) gave release rates of:
8 and 0 mg Cu per day over 28 days
6 and 9 mg Cu per day over 56 days
6 and 0 mg Cu per day over 87 days

EXAMPLE 20

Nine cylindrical devices (24 mm×12 mm) of the cement shown on page 47 were provided. Three devices (A, B, C) were analysed for initial copper and cobalt content and the remainder (D to I) were placed in the reticulum of a cow having a fistulated rumen.

The results are shown in Table 17.

TABLE 17

| Device | Weight (g) | Cu content (g) | Cu content (%) | Co content (mg) | Co content (%) |
|---|---|---|---|---|---|
| A | 15.63 | 5.10 | 32.6 | 306 | 1.96 |
| B | 15.84 | 5.24 | 33.0 | 288 | 1.82 |
| C | 15.51 | 5.08 | 32.7 | 290 | 1.87 |

| Device | Days | Wt. change | Cu loss (g) | Cu loss (mg/day) | Co change (mg) | Co change (mg/day) |
|---|---|---|---|---|---|---|
| D | 29 | +4% | 0.50 | 17.2 | −37 | −1.3 |
| E | 29 | +2% | 0.06 | 2.1 | −28 | −1.0 |
| F | 63 | +6% | 0.23 | 3.7 | +32 | +0.5 |
| G | 63 | +8% | 0.11 | 1.7 | +6 | 0 |
| H | 106 | +5% | 0.46 | 4.3 | +1 | 0 |
| I | 106 | +4% | 0.23 | 2.2 | +3 | 0 |

EXAMPLE 21

Seven cylindrical devices 24 mm×12 mm of the cement shown on page 47 but comprising $Co^{58}$ were given, one each, by mouth to sheep. The sheep were radiocounted at intervals after administration. One was then slaughtered after 29 days; another after 93 days. In both cases the device was recovered and the radioactivity of the carcass, recovered device, liver and gastrointestinal tract was measured. Approximately 1% of the total radioactivity remained after removal of the device:

one third in the carcass and two thirds in the gastrointestinal tract.

Initial results are shown in Table 18.

TABLE 18

| Cobalt loss from pellets | 29 days | 93 days |
|---|---|---|
| Loss by in vivo count | 26% | 23% |
| Loss by in vitro count | 25% (0.79 mg/day) | 23% (0.33 mg/day) |
| Loss by analysis (at. Abs.) | 0 (gain of 12 mg) | 20% (0.29 mg/day) |
| Loss of Cu (by analysis) | 0.25 g (13%) | 0.65 g (39%) |
| mg Cu/day | 6.4 | 7.0 |
| Weight loss | 12% | 4% |

Continuing experimentation has shown an approximately constant rate of release of cobalt to a maximum of 160 to 210 days (depending on host) with a release of up to 65% of the cobalt. An average rate of release was approximately 0.5 mg Co/day.

EXAMPLE 22

In this Example, livestock of Warren Farm, Lambourn, Berkshire, an area natrually deficient in selenium and copper, was divided into four groups, the first being a control and receiving no trace element supplement; the second receiving injected trace element supplement; the third receiving a proprietary prepartion; and the fourth receiving devices of the invention as used in Example 21 but also comprising kaolin. The livestock comprised yearling Hereford×Friesian steers.

A significant increase in carcass weight, up to 20 kg in the cattle, was found in the cattle.

We claim:

1. A sustained release formed composition, which comprises a source of at least one trace chemical element selected from the group consisting of selenium, cobalt and iodine incorporated into a phosphate cement and sustainedly releasable therefrom on contact with an aqueous medium.

2. A sustained release formed composition according to claim 1 wherein said at least one trace chemical element is an intrinsic component of the cement.

3. A sustained release formed composition according to claim 1 wherein said at least one trace chemical element is dispersed in the cement.

4. A formed composition according to claim 1 which also comprises at least one active substance other than a trace chemical element.

5. A formed composition according to claim 4 wherein the at least one active substance other than a trace chemical element is a substance having a medicinal effect.

6. A formed composition according to claim 1 which is in a dosage form.

7. A formed composition according to claim 1 which includes a weighting agent.

8. A formed composition according to claim 1 which is a cylindrical dosage form.

9. A process for the preparation of a formed composition according to claim 1, which process comprises preparing a cement-forming mixture in which is incorporated a source of at least one trace chemical element selected from the group consisting of selenium, cobalt and iodine; investing a mould with the mixture; and permitting the cement-forming mixture to cure in the mould.

10. A process according to claim 9 wherein the cement is subjected to a post-curing treatment at an elevated temperature.

11. A particulate composition comprising a trace chemical element selected from the group consisting of selenium, cobalt and iodine and phosphate cement-forming materials reactable in the presence of a polar liquid to form a formed composition according to claim 1.

12. A particulate composition according to claim 11 wherein the polar liquid comprises water.

13. A pack which comprises a particulate composition comprising a trace chemical element selected from the group consisting of selenium, cobalt and iodine and phosphate cement-forming materials, a polar liquid reactable with the composition to form a formed composition according to claim 1, and separating means to prevent accidental reaction of the particulate composition with the polar liquid.

14. A formed composition according to claim 1, wherein said phosphate cement is an acid phosphate cement.

* * * * *